(12) United States Patent
Green et al.

(10) Patent No.: US 9,701,625 B2
(45) Date of Patent: Jul. 11, 2017

(54) NITRONE COMPOUNDS AND THEIR USE IN PERSONAL CARE

(71) Applicant: Dow Global Technologies LLC, Midland, MI (US)

(72) Inventors: George D. Green, Cary, IL (US); Raymond J. Swedo, Mount Prospect, IL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/120,757

(22) PCT Filed: Mar. 5, 2015

(86) PCT No.: PCT/US2015/018846
§ 371 (c)(1),
(2) Date: Aug. 23, 2016

(87) PCT Pub. No.: WO2015/134688
PCT Pub. Date: Sep. 11, 2015

(65) Prior Publication Data
US 2016/0362361 A1 Dec. 15, 2016

Related U.S. Application Data

(60) Provisional application No. 61/949,680, filed on Mar. 7, 2014.

(51) Int. Cl.
*C07C 291/02* (2006.01)
*A61K 8/41* (2006.01)
*A61Q 19/08* (2006.01)

(52) U.S. Cl.
CPC .......... *C07C 291/02* (2013.01); *A61K 8/416* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 5,176,983 A | 1/1993 | Horn et al. | |
| 5,273,863 A | 12/1993 | Horn et al. | |
| 5,455,272 A | 10/1995 | Janzen et al. | |
| 6,002,001 A | 12/1999 | Carney et al. | |
| 7,655,251 B2 | 2/2010 | Durand et al. | |
| 2010/0168112 A1 | 7/2010 | Kelly et al. | |
| 2012/0058088 A1 | 3/2012 | Sardi | |

FOREIGN PATENT DOCUMENTS

| | | |
|---|---|---|
| CN | 102153498 A | 8/2011 |
| DE | 10201223 A1 | 7/2003 |
| EP | 1284133 A1 | 2/2003 |
| EP | 1591104 A1 | 11/2005 |
| ES | 2316312 A1 | 4/2009 |
| IN | 1377CHE2009 | 8/2012 |
| JP | 2011251914 A | 12/2011 |
| WO | 9222290 A1 | 12/1992 |
| WO | 02065993 A2 | 8/2002 |
| WO | 2005041905 A2 | 5/2005 |
| WO | 2005087214 A1 | 9/2005 |
| WO | 2009108999 A1 | 9/2009 |
| WO | 2011130400 A1 | 10/2011 |
| WO | 2012150370 A1 | 11/2012 |
| WO | 2013081778 A2 | 6/2013 |

OTHER PUBLICATIONS

Database CAPLUS in STN, Acc. No. 2005:405402, Lupia et al., WO 2005/041905 A2 (May 12, 2005) (abstract).*
Database CAPLUS in STN, Acc. No. 1993:116773, Carney et al., WO 92/22290 A1 (Dec. 23, 1992) (abstract).*
Database CAPLUS in STN, Acc. No. 1998:770325, Kliegel et al., Canadian Journal of Chemistry (1998), 76(7), pp. 1082-1092 (abstract).*
Kliegel et al., Canadian Journal of Chemistry (1998), 76(7), pp. 1082-1092.*
Wang, M. et al; Journal of Agricultural and Food Chemistry, 1999, vol. 47, No. 10, pp. 3974-3977.
Hung, Chi-Feng, et al; Biol Pharm. Bull, 31(5) , 2009, pp. 955-962.
Fabris, S., et al; Biophysical Chemistry, 135, 2008, pp. 76-83.
Fang, J-G, et al; Journal of Agricultural and Food Chemistry, 2008, vol. 56, pp. 11458-11463.
Lee, Soo-Jin, Kim, Moon-Moo; Life Sciences, 2011, vol. 88, pp. 465-472.
Re, R. et al; Free Radical Biology & Medicine, 1999, vol. 26, No. 9/10, pp. 1231-1237.
Samadi, A., et al; Bioorganic & Medicinal Chemistry, 2011, vol. 19, No. 2, pp. 951-960.
Hill, R.; Spin Traps: The New Anti-Oxidant?; Beautymagonline [Retrieved Mar. 29, 2013], Retrieved From the Internet <URL:http://www.beautymagonline.com/beauty-articles-4/1112-spin-traps-2>, pp. 1-3.
Perricone, N., The Wrinkle Cure: The Formula for Stopping Time, Vintage/Ebury (A Division of Random); Illustrated Edition, pp. 182-186, Jul. 1, 2001.

(Continued)

Primary Examiner — Brian J Davis
(74) Attorney, Agent, or Firm — Edward L. Brant

(57) ABSTRACT

Provided are compounds and compositions thereof that are useful as antioxidants in personal care formulations. The compounds are of the Formula I:

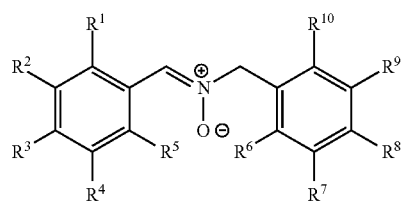

wherein $R^1$, $R^2$, $R^3$, $R^4$, $R^5$, $R^6$, $R^7$, $R^8$, $R^9$, and $R^{10}$ are independently H, $C_1$-$C_{10}$ alkyl, —OH, $C_1$-$C_6$ alkoxy, —COOH, —COO⁻M⁺, or —O⁻M⁺, where M⁺ is a sodium, potassium, or ammonium ion, provided that at least one of $R^6$, $R^7$, $R^8$, $R^9$, or $R^{10}$ is —OH.

11 Claims, No Drawings

(56) References Cited

OTHER PUBLICATIONS

Croitour, M D. "Nitrones are Able to Release Nitric Oxide in Aqueous Environment Under Hydroxyl Free Radical Attack", Nitric Oxide: Biology and Chemistry, vol. 25, No. 3, pp. 309-315, 2011.
Scott, G. "Mechanisms of Antioxidant Action: Rubber Bound Antioxidants Based on Nitrones-1, Non-Sulphur Vulcanizates", European Polymer Journal, vol. 14, pp. 905-912, Pergamon Press Ltd 1978.
Floyd, R. "Nitrones, Their Value as Therapeutics and Probes to Understand Aging", Mechanisms of Aging and Development 123, pp. 1021-1031, 2002.
Hensley, K. "Nitrone-Based Free Radical Traps as Neuroprotective Agents in Cerebral Ischaemia and Other Pathologies", IRN 40, Chapter 13, pp. 299-317, Academic Press Limited, 1997.
Bagheri, R. "Mechanisms of Antioxidant Action: Evidence for a Regenerative Cycle During the Melt Stabilisation of Polypropylene by Galvinoxyl", Polymer Degradation and Stability, vol. 5, pp. 145-160, 1983.
Finlayson, M. "Aging With Multiple Sclerosis", J. Neurosci Nurs. vol. 36, Issue 5, pp. 1-10, 2004.
Zou, et al; Fabrication of Surface-Modified CDSE Quantum Dots by Self-Assembly of a Functionalizable Comb Polymer, Polymer International, vol. 5, Issue 60, pp. 751-757, 2011.
Kasiotis, et al; Reservatrol and Related Stilbenes: Their Anti-Aging and Anti-Angiogenic Properties; Food and Chemical Technology, vol. 61, pp. 112-120, 2013.
Burgess, C.M.; Cosmetic Dermatology, p. 19, 2005.

\* cited by examiner

NITRONE COMPOUNDS AND THEIR USE IN PERSONAL CARE

FIELD OF THE INVENTION

This invention relates generally to compounds and compositions that are useful as antioxidants in personal care formulations. The compounds contain both nitrone and phenolic functionalities.

BACKGROUND

Personal care compositions are important products for most consumers. Personal care compositions contain a variety of additives that provide a wide array of benefits to the composition.

Antioxidants are among the additives commonly used in personal care compositions. Antioxidants help protect the skin from the damaging effects of free radicals caused by various environmental stresses, such as exposure to UV rays. Free radicals include, for example, singlet oxygen. Free radicals cause damage to the skin with the end result being a loss of elasticity of the skin and the appearance of wrinkles leading to premature aging of the skin.

Based on the physiological mechanism of the aging process, oxidative stress due to increased level of reactive oxygen species (ROS) especially caused by physiological stress or solar ultraviolet radiation can accelerate skin aging. There is evidence that intrinsic and extrinsic aging (i.e., photoaging) have several overlapping biochemical and molecular mechanisms. Type I collagen constitutes the major structural component of dermal connective tissue and provides dermis with tensile strength and stability. Degradation of collagen in the dermis has been reported in intrinsic aged and photoaged skin. Additionally, a major signaling pathway contributing to photoaging by ROS is the up-regulation of matrix metalloproteinase-1 (MMP-1), which leads to degradation of dermal collagen, associated with aging spots and wrinkles. Therefore, stronger antioxidants are needed as potential anti-aging ingredients to provide protection.

One such antioxidant that has been studied, as disclosed in WO 2012/150370, is resveratrol (3,5,4'-trihydroxy-trans-stilbene). Resveratrol is a naturally occurring polyphenolic compound found in the skin of grapes and other fruits. It has been investigated in the context of its potential chemopreventive properties against skin damage from UV exposure and against ROS induced damage associated with brain function, heart disease, and cancer. However, the natural abundance of resveratrol is low, and it is thus very expensive.

Consequently, there is a need to develop new antioxidant compositions, for use in personal care, including compositions that mitigate degradation of collagen in skin.

STATEMENT OF INVENTION

We have now found that nitrone compounds of Formula I have equivalent efficacy as radical scavengers at lower concentrations (as measured by duration of antioxidant protection), or higher efficacy (less oxidative damage and/or longer antioxidant protection) at equivalent concentrations as compared to conventional antioxidants. It has also been found that the performance of nitrones cannot be achieved by simply adding two different antioxidants, e.g., one with a phenolic functionality and another with nitrone functionality. Rather, the presence of both functionalities in the same molecule is an important aspect of their favorable performance.

Accordingly, one aspect of the invention provides a compound of Formula I:

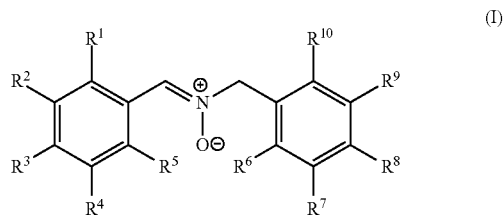

wherein $R^1$, $R^2$, $R^3$, $R^4$, $R^5$, $R^6$, $R^7$, $R^8$, $R^9$, and $R^{10}$ are independently H, $C_1$-$C_{10}$ alkyl, —OH, $C_1$-$C_6$ alkoxy, —COOH, —COO$^-$M$^+$, or —O$^-$M$^+$, where M$^+$ is a sodium, potassium, or ammonium ion, provided that at least one of $R^6$, $R^7$, $R^8$, $R^9$, or $R^{10}$ is —OH. In certain preferred embodiments, at least two of $R^1$, $R^2$, $R^3$, $R^4$, $R^5$, $R^6$, $R^7$, $R^8$, $R^9$, or $R^{10}$ are —OH.

Another aspect of the invention provides a personal care composition comprising (a) an antioxidant compound of Formula I, and (b) a dermatologically acceptable carrier.

In another aspect, the invention provides a cosmetic method of treating skin which comprises applying to the skin a composition as described herein.

In a still further aspect, there is provided a method for inhibiting the degradation of collagen, the method comprising topically administering to skin an effective amount of a composition as described herein.

In a yet further aspect, there is provided a method for reducing the visible signs of aging, the method comprising applying to skin in need of such treatment a composition as described herein.

DETAILED DESCRIPTION

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

"Room temperature," as used in this specification, is the ambient temperature, for example, 20-25° C.

"Alkyl," as used in this specification, encompasses straight and branched chain aliphatic hydrocarbon groups having the indicated number of carbon atoms. If no number is indicated, then 1-6 alkyl carbons are contemplated. Unless otherwise indicated, the alkyl group is optionally substituted with 1, 2, or 3, preferably 1 or 2, more preferably 1, substituents that are compatible with the syntheses described herein. Such substituents include, but are not limited to, nitro, halogen, carboxylic acids (e.g., $C_0$-$C_6$—COOH), $C_2$-$C_6$ alkene, cyano, amido, and/or ester. Unless otherwise indicated, the foregoing substituent groups are not themselves further substituted.

As noted above, in one aspect the invention provides a compound of Formula I. In another aspect, the invention provides a composition comprising a compound of Formula I and a dermatologically acceptable carrier.

In some embodiments, at least three of $R^1$, $R^2$, $R^3$, $R^4$, $R^5$, $R^6$, $R^7$, $R^8$, $R^9$, or $R^{10}$ in the compounds of Formula I are —OH. In some embodiments, at least four of $R^1$, $R^2$, $R^3$, $R^4$, $R^5$, $R^6$, $R^7$, $R^8$, $R^9$, or $R^{10}$ in the compounds of Formula I are —OH.

In some embodiments, at least two of $R^6$, $R^7$, $R^8$, $R^9$, or $R^{10}$ are —OH.

In some embodiments, $R^8$ is —OH, and at least one of $R^6$, $R^7$, $R^9$ or $R^{10}$ is —OH.

In some embodiments, $R^8$ is —OH, at least one of $R^6$, $R^7$, $R^9$ or $R^{10}$ is —OH, and none of $R^1$, $R^2$, $R^3$, $R^4$, $R^5$, $R^6$, $R^7$, $R^9$, or $R^{10}$ are $C_1$-$C_6$ alkoxy.

In some embodiments, at least one of $R^1$ or $R^5$ is —OH.

In some embodiments, at least one of $R^6$, $R^8$, or $R^{10}$ is —OH.

In some embodiments, $R^2$ and/or $R^4$ is H, OH, or $C_1$-$C_6$ alkoxy (preferably methoxy).

In some embodiments of the composition of the invention, the compound of Formula I is as shown in Table 1:

TABLE 1

Specified Compounds of Formula I

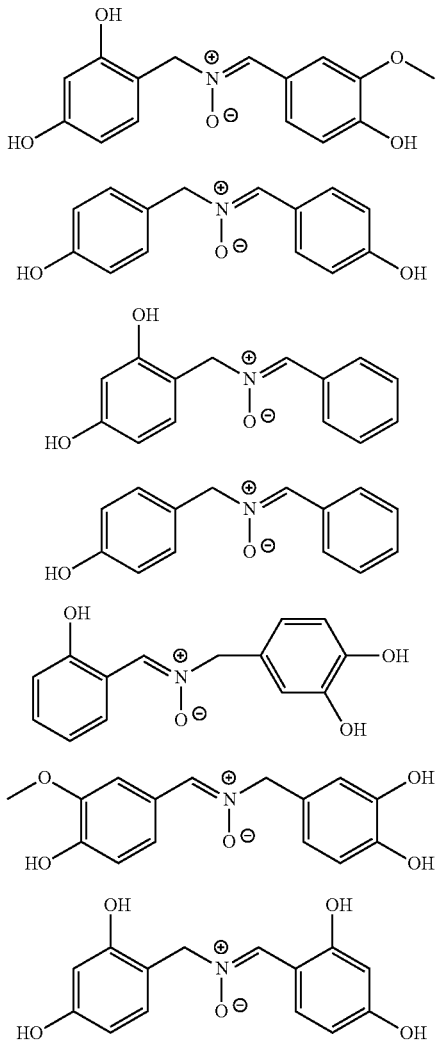

A person of ordinary skill in the art can readily determine the effective amount of the antioxidant compound of Formula I that should be used in a particular composition in order to provide the benefits described herein (e.g., free radical scavenging and inhibition of collagen degradation), via a combination of general knowledge of the applicable field as well as routine experimentation where needed. By way of non-limiting example, the amount of the compound of Formula I in the composition of the invention may be in the range of from 0.01 to 5 weight percent, preferably from 0.05 to 3 weight percent, and more preferably from 0.1 to 1 weight percent, based on the total weight of the composition.

Compounds of Formula I may be readily prepared by those skilled in the art using known synthetic techniques. For instance, the compounds may be prepared by the reaction of a phenyl aldehyde compound (containing one or more hydroxyl groups on the phenyl, such as 4-hydroxybenzaldehyde) with a phenylhydroxylamine compound (also containing one or more hydroxyl groups on the phenyl, such as 3,4-dihydroxybenzylhydroxylamine), followed by isolation and purification of the desired product.

Compositions of the invention also include a dermatologically acceptable carrier. Such material is typically characterized as a carrier or a diluent that does not cause significant irritation to the skin and does not negate the activity and properties of active agent(s) in the composition. Examples of dermatologically acceptable carriers that are useful in the invention include, without limitation, emulsions, creams, aqueous solutions, oils, ointments, pastes, gels, lotions, milks, foams, suspensions, powders, or mixtures thereof. In some embodiments, the composition contains from about 99.99 to about 50 percent by weight of the dermatologically acceptable carrier, based on the total weight of the composition.

The dermatologically acceptable carrier of the invention may also include, for instance, water, a thickener, an emollient, an emulsifier, a humectant, a surfactant, a suspending agent, a film forming agent, a foam building agent, a preservative, an antifoaming agent, a fragrance, a lower monoalcoholic polyol, a high boiling point solvent, a propellant, a colorant, a pigment, glycerin, a mineral oil, silicon feel modifiers, preservatives, emollients, or mixtures thereof.

Other additives may be included in the compositions of the invention such as, but not limited to, abrasives, absorbents, aesthetic components such as fragrances, pigments, colorings/colorants, essential oils, skin sensates, astringents (e.g., clove oil, menthol, camphor, eucalyptus oil, eugenol, menthyl lactate, witch hazel distillate), anti-caking agents, antifoaming agents, antimicrobial agents (e.g., iodopropyl butylcarbamate), other antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, thickeners, and vitamins (e.g., Vitamin C) and derivatives thereof.

The composition of the invention may be, for example, in the form of an oil, a gel, a solid stick, a lotion, a cream, a milk, an aerosol, a spray, a foam, a mousse, an ointment or a fatty ointment or a powder.

Compositions of the invention may be used in a variety of personal care applications, such as in cosmetics and in skin care (e.g., lotions, creams, oils, topical medicines, and sunscreens).

The compositions of the invention may be manufactured by processes well known in the art, e.g., by means of conventional mixing, dissolving, granulating, emulsifying, encapsulating, entrapping or lyophilizing processes.

As noted above, compositions of the invention, containing a compound of Formula I, are highly effective as radical scavengers. They exhibit significantly better antioxidant attributes compared to previously known antioxidants for personal care applications. Furthermore it has been found that the performance of nitrones that have phenolic groups cannot be achieved by simply adding two different antioxidants, one with a phenolic functionality and another with nitrone functionality. Rather, the presence of both functionalities in the same molecule is an important aspect of their favorable performance.

The cosmetic compositions of the invention are useful for the treatment and protection of skin from free radicals caused, for instance, by exposure to ultraviolet light, such as UVA and UVB rays, as well as other harmful forms of radiation, such as long wave infrared.

Thus, for instance, the cosmetic compositions may be used in a method for inhibiting the degradation of collagen. According to such method, an effective amount of the composition may be topically administering to skin in need of such treatment.

The compositions may also be used in a method for reducing the visible signs of aging, which may result from the radical induced degradation of collagen in the skin, by applying to skin in need of such treatment the composition. Visible signs of aging may include, for instance, development of textural discontinuities such as wrinkles and coarse deep wrinkles, skin lines, crevices, bumps, large pores, or unevenness or roughness, reducing fine lines, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, and other histological changes in the stratum corneum, dermis, epidermis, the skin vascular system (e.g., telangiectasia or spider vessels), and underlying tissues, especially those proximate to the skin.

In practicing the methods of the invention, the cosmetic composition are generally administered topically by applying or spreading the compositions onto the skin. A person of ordinary skill in the art can readily determine the frequency with which the cosmetic compositions should be applied. The frequency may depend, for example, on the amount of sunlight that an individual is likely to encounter in a given day and/or the sensitivity of the individual to sunlight. By way of non-limiting example, administration on a frequency of at least once per day may be desirable.

Some embodiments of the invention will now be described in detail in the following Examples.

EXAMPLES

Example 1

Synthesis of the Oxime Precursor
3,4-Dihydroxybenzaldehyde Oxime (34DHBzOx)

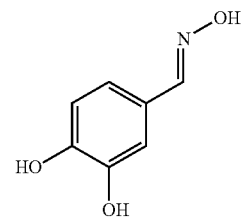 [SMILES: O/N=C/c1ccc(O)c(O)c1]

A 100 mL 3-neck flask was equipped with a magnetic stirrer, a reflux condenser, an addition funnel, a thermocouple, an ice bath, and a nitrogen blanket. The flask was charged with 13.81 grams (0.10 moles) of 3,4-dihydroxybenzaldehyde and with 50 mL of 100% ethanol. The mixture was stirred at room temperature under nitrogen to give a clear dark brown solution. The solution was cooled to <15° C. The addition funnel was charged with 6.63 grams (0.10 moles) of 50 wt. % aqueous hydroxylamine solution. The hydroxylamine solution was added to the cooled aldehyde solution over a period of about 45 minutes. During the addition, the reaction mixture temperature was maintained at <20° C. After completing the hydroxylamine solution addition, the reaction mixture was heated at 55° C. until GC analysis showed that the aldehyde was essentially gone (about 7 hours). The reaction mixture was solvent-stripped by rotary evaporation to give a quantitative yield of the oxime as a brown solid. M.P.=161-163° C. GC showed >98% purity. Structure was confirmed by IR, NMR, and GC/MS analyses.

Example 2

Synthesis of the Hydroxylamine Precursor
4-((Hydroxyamino)methyl)benzene-1,3-diol
(34DHBzHA)

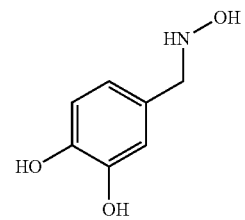

A 125 mL 3-neck flask was equipped with a magnetic stirrer, a sintered glass sparging tube, a pH electrode with meter, and a Claisen adapter fitted with a thermocouple and a gas outlet. The flask was charged with 4.59 grams (0.03 moles) of the 3,4-dihydroxybenzaldehyde oxime (34DHBzOx) from above and with 40 mL of methanol. The mixture was stirred at room temperature to give a clear brown solution. Sodium cyanoborohydride (1.89 grams, 0.03 moles) was then added to the oxime solution in one portion. A lecture bottle of hydrogen chloride gas was connected to the sparging tube with a safety trap in between. The HCl bottle was opened just enough to allow a trickle of gas to sparge into the reaction mixture. The pH of the mixture dropped quickly from about 7 to <3. At the same time, the reaction mixture foamed vigorously and solids began to precipitate. Sparging with HCl was stopped, and the pH was monitored. After the pH had stabilized at ≤3 for 1 hour, the reaction mixture was filtered and the white solids were washed on the filter with small portions of methanol. After drying, 1.38 grams of white solid were obtained. The filtrate and methanol washings were combined, and the solvent was removed by rotary evaporation to give 6.27 grams of beige solids. These solids were combined with the solids obtained by filtration, and were dissolved in about 25 mL of water to give a clear brown solution having pH about 5. The pH was increased to about 8 by the addition of a saturated aqueous solution of sodium bicarbonate. At this point, solids began to separate out. The mixture was cooled in an ice bath for about 1 hour, then it was filtered. The solids were washed on the filter with portions of water. After drying under vacuum at 55° C. for about 1 hour, the yield of hydroxylamine as a dark brown solid was 2.56 grams (55% yield). MP=149-151° C. The structure was confirmed by IR and NMR analyses. HPLC analysis gave a purity of >75%.

Example 3

Synthesis of the Nitrone 1-(3,4-Dihydroxyphenyl)-N-(4-hydroxy-3-methoxybenzylidene)methanamine oxide (VAN-34DHBzHA)

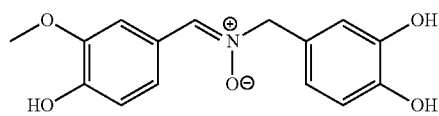 [SMILES: COc1cc(/C=[N+](\[O-])Cc2ccc(O)c(O)c2)ccc1O]

A 500 mL 1-neck flask was equipped with a magnetic stirrer and a septum. The flask was charged with 7.76 grams (0.05 moles) of 3,4-dihydroxybenzylhydroxylamine, 175 mL of methanol, and 7.61 grams (0.05 moles) of vanillin. The reaction mixture was stirred at room temperature for 2 days. The solvent was removed from the reaction mixture by rotary evaporation to give 14.52 grams of light brown solid product (100% of theory). MP=about 129° C. to >150° C. HPLC analysis gave a purity of about 94%.

A 4.22 gram sample of the crude product was purified by column chromatography on 115 grams of silica gel 60, using ethyl acetate—methanol (95:5, v/v) as the eluting solvent system. The column fractions were monitored by TLC. The yield of purified product obtained was 1.10 grams (26% based on amount charged to the column). MP=190-191° C. Structure was confirmed by IR, NMR, and GC/MS analyses. HPLC analysis gave a purity of >99%.

Example 4

Synthesis of the Nitrone 1-(3,4-dihydroxyphenyl)-N-(2-hydroxybenzylidene)methanamine oxide (SAL-34DHBzHA)

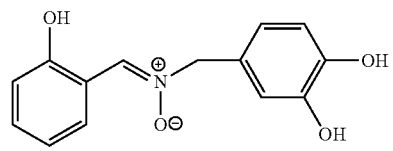 [SMILES: [O-]/[N+](=C\c1ccccc1O)Cc1ccc(O)c(O)c1]

A 250 mL 1-neck flask was equipped with a magnetic stirrer and a septum. The flask was charged with 3.88 grams (0.025 moles) of 3,4-dihydroxybenzylhydroxylamine, 75 mL of methanol, and 3.05 grams (0.025 moles) of salicylaldehyde. The reaction mixture was stirred at room temperature for 3 days. The solvent was removed from the reaction mixture by rotary evaporation to give 11.86 grams of dark brown tarry product (180% of theory). The crude product was stirred at room temperature with 100 mL of methanol; not all of the product dissolved. The mixture was filtered. The solvent was removed from the filtrate by rotary evaporation to give 7.59 grams of brown solid product (117% of theory). HPLC analysis showed about 87 area % product with both higher and lower molecular weight impurities also present.

A 4.15 gram sample of the crude product was purified by column chromatography on 100 grams of silica gel 60, using ethyl acetate—methanol (95:5, v/v) as the eluting solvent system. The column fractions were monitored by TLC. The yield of purified product obtained was 1.51 grams (36% based on amount charged to the column). MP=157-161° C. Structure was confirmed by IR, NMR, and GC/MS analyses.

Example 5

Synthesis of the Nitrone 1-(2,4-dihydroxyphenyl)-N-(4-hydroxy-3-methoxybenzylidene)methanamine oxide (VAN-24DHBzHA)

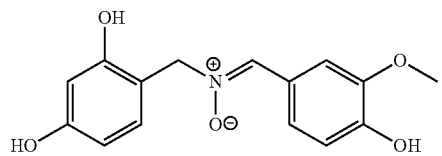 [SMILES: COc1cc(/C=[N+](\[O-])Cc2ccc(O)cc2O)ccc1O]

A 100 mL 1-neck flask was equipped with a magnetic stirrer and a rubber septum. The flask was charged with 1.05 grams (0.0068 moles) of 4-((Hydroxyamine)methyl)benzene-2,4-diol, 1.1 grams (0.0072 moles) of vanillin, and 20 mL of methanol. Not all of the solids dissolved, even after heating at 50° C. for 2 hours. The mixture was stirred at room temperature for 3 days. The mixture was filtered, and the solids were washed on the filter with a little methanol. After drying in air for several hours, the yield of product was 1.7 grams (87% yield). MP=175-177° C. Structure was confirmed by IR and NMR analyses.

Example 6

Synthesis of the Nitrone N-(4-hydroxybenzylidene)-1-(4-hydroxyphenyl)methanamine oxide (pHBz-pHBzHA)

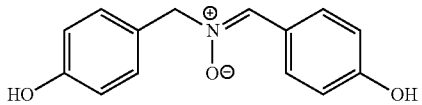 [SMILES: [O-]/[N+](=C\c1ccc(O)cc1)Cc1ccc(O)cc1]

A 100 mL 1-neck flask was equipped with a magnetic stirrer and a rubber septum. The flask was charged with 1.6 grams (0.01 moles) of p-hydroxybenzylhydroxyamine hydrochloride, 0.36 grams (0.1 moles) of sodium hydroxide pellets, and 10 mL of methanol. As the mixture was stirred at room temperature, sodium chloride began to precipitate. Water was added until a homogeneous solution was obtained. About 4 mL were required. The p-hydroxy benzaldehyde (1.2 grams, 0.01 moles) was then added, and the clear solution was heated at 60° C. for 6 hours. The mixture was then stirred at room temperature for 3 days. The resulting white slurry was filtered, and the solids were washed on the filter with a little water. After drying under vacuum at 35° C., the yield of product was 1.8 grams (79.3% yield). MP=196-196° C. Structure was confirmed by IR and NMR analyses.

Example 7

Synthesis of the Nitrone N-benzylidene-1-(2,4-dihydroxyphenyl)methanamine oxide (Bz-24DHBzHA)

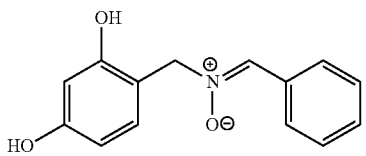 [SMILES: [O-]/[N+](=C\c1ccccc1)Cc1ccc(O)cc1O]

A 100 mL 1-neck flask was equipped with a magnetic stirrer and a rubber septum. The flask was charged with 1.55 grams (0.01 moles) of 2,4-dihydroxybenzylhydroxlamine, 1.06 grams (0.01 moles) of benzaldehyde, 10 mL of methanol, and 2 mL of water. The mixture was stirred at 50° C. for 2 hours, yielding a clear brown solution. The mixture was stirred at room temperature overnight. The resulting slurry was filtered. The solids were washed on the filter with a little warm water, then they were dried under vacuum at 35° C. The yield of product was 1.65 grams (67.9% yield). MP=158° C. Structure was confirmed by IR and NMR analyses.

Example 8

Synthesis of the Nitrone N-benzylidene-1-(4-hydroxyphenyl)methanamine oxide (Bz-pHBzHA)

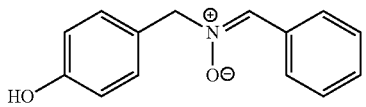 [SMILES: [O-]/[N+](=C\c1ccccc1)Cc1ccc(O)cc1]

A 100 mL 1-neck flask was equipped with a magnetic stirrer and a rubber septum. The flask was charged with 1.39 grams (0.01 moles) of p-hydroxybenzylhydroxlamine, 1.06 grams (0.01 moles) of benzaldehyde, 10 mL of methanol, and 2 mL of water. The mixture was heated at 50° C. for 6 hours, and then it was stirred at room temperature overnight. The resuling white slurry was filtered, and the solids were washed on the filter with a small amount of water. The solids were dried under vacuum at 35° C. The yield of product was 1.8 grams (79% yield). MP=191° C. Structure was confirmed by IR and NMR analyses.

Example 9

Synthesis of the Nitrone N-(2,4-dihydroxybenzylidene)-1-(2,4-dihydroxyphenyl)methanamine oxide (24DHBz-24DHBzHA)

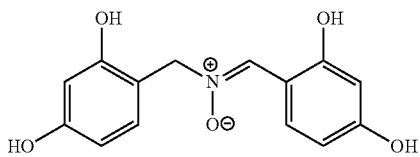 [SMILES: [O-]/[N+](=C\c1ccc(O)cc1O)Cc1ccc(O)cc1O]

A 100 mL 1-neck flask was equipped with a magnetic stirrer and a rubber septum. The flask was charged with 1.55 grams (0.01 moles) of 2,4-dihydroxybenzylhydroxylamine, 1.38 grams (0.01 moles) of 2,4-dihydroxybenzaldehyde, 10 mL of methanol, and 2 mL of water. The mixture was heated at 50° C. for 6 hours, and then it was stirred at room temperature overnight. The resuling white slurry was filtered, and the solids were washed on the filter with a small amount of water. The solids were dried under vacuum at 35° C. The yield of product was 2.4 grams (87% yield). MP=203-204° C. Structure was confirmed by IR and NMR analyses.

Example 10

Antioxidant Potential

Antioxidant potential is evaluated using the Oxygen Radical Absorbance Capacity (ORAC) protocol. ORAC is a chemical in-vitro method based on the hydrogen atom transfer (HAT) mechanism (see N. Re et al., *Free Radical Biology & Medicine*, 26 (9/10), 1231 (1997)). ORAC measures antioxidant inhibition of peroxyl radical induced oxidations and thus reflects classical radical chain breaking antioxidant activity by H atom transfer. In this assay, the peroxyl radical reacts with a fluorescent probe to form a non-fluorescent product. This is quantitated using a fluorescence measurement. Antioxidant capacity is determined by decreased rate and amount of product formed over time. This assay depends upon the free radical damage to the fluorescent probe resulting in the change in its fluorescence intensity. The change of fluorescence intensity is an indicator of the degree of free radical damage. In the presence of an antioxidant, the inhibition of free radical damage is reflected in higher fluorescence intensity and can be measured as antioxidant capacity against the free radicals. The uniqueness of ORAC assay is that the reaction is driven to completion. This allows calculation of the area under the curve (AUC) and gives an absolute quantitation of antioxidancy as opposed to relative measurements in many other assays.

As noted, the longer it takes to observe a decrease in fluorescence, the higher the antioxidant (AO) potential. From the AUC for a given antioxidant, the AUC for blank is subtracted to give its ORAC value. The concentration of AO needed to give the same AUC values as Trolox is calculated and used to represent the Trolox equivalent AO Capacity (TEAC). Trolox is ((±)-6-Hydroxy-2,5,7,8-tetramethylchromane-2-carboxylic acid, CAS #53188-07-1), and is used as an internal control.

The ORAC test is conducted in the compounds of Table 1 above (inventive compounds) as well as to Vitamin C, Vitamin E, and the following comparative compounds:

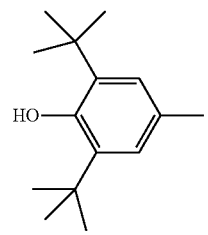

Butylated hydroxytoluene (BHT)

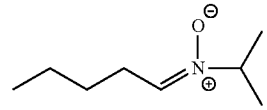

(Z)-N-pentylidenepropan-2-amine oxide (VAL-IPHA)

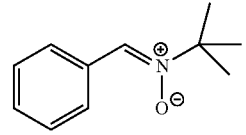

2-Phenyl-N-tert-butylnitrone (PBN)

The inventive nitrones in the ORAC test solutions were at a concentration of 30 micromolar, while the concentrations of Trolox, Vitamin C, Vitamin E, BHT, PBN+BHT, and VAL-IPHA were at 100 micromolar. The TEAC values calculated from the ORAC values are listed the Table 2.

TABLE 2

| TEAC Values | | |
|---|---|---|
| ANTIOXIDANT COMPOUND | EXAMPLE NITRONE | TEAC |
| Vitamin C (comparative) | — | 0.76 |
| Vitamin E (comparative) | — | 0.13 |
| BHT (comparative) | — | 0.11-0.21 |
| PBN + BHT (comparative) | — | 0.24 |
| VAL-IPHA (comparative) | — | 0.18 |
| (inventive) | 1 | 6.45 |
| (inventive) | 2 | 2.94 |
| (inventive) | 3 | 10.01 |

TABLE 2-continued

TEAC Values

| ANTIOXIDANT COMPOUND | EXAMPLE NITRONE | TEAC |
|---|---|---|
| (structure) (inventive) | 4 | 8.31 |
| (structure) (inventive) | 5 | 13.26 |
| (structure) (inventive) | 6 | 5.23 |
| (structure) (inventive) | 7 | 9.88 |

Surprisingly, it is found that the compounds of the invention displayed significantly higher ORAC values compared to the known antioxidants Vitamin E or C. It is also evident that the TEAC values of phenolic AOs such as BHT, a non-aromatic nitrone such as VAL-IPHA, or an aromatic nitrone such as PBN are not very high compared to the TEAC values of the compounds of the invention, which contain both phenolic and nitrone moieties in a polyhydroxy stilbenoid mimic structure. The TEAC value for a physical blend of an aromatic nitrone and a phenolic AO (PBN+BHT) is relatively small also. This leads us to believe that for the regenerative mechanism to take place, the nitrone and the phenolic functionalities need to be part of the same molecule.

What is claimed is:

1. A compound of Formula I:

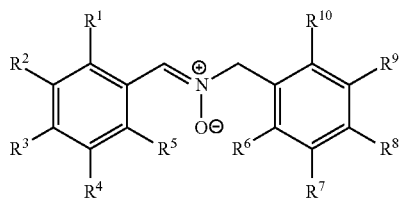

(I)

wherein $R^1$, $R^2$, $R^3$, $R^4$, $R^5$, $R^6$, $R^7$, $R^8$, $R^9$, and $R^{10}$ are independently H, $C_1$-$C_{10}$ alkyl, —OH, $C_1$-$C_6$ alkoxy, —COOH, —COO$^-$M$^+$, or —O$^-$M$^+$, where M$^+$ is a sodium, potassium, or ammonium ion, provided that at least three of $R^1$, $R^2$, $R^3$, $R^4$, $R^5$, $R^6$, $R^7$, $R^8$, $R^9$, or $R^{10}$ are —OH, wherein at least one of $R^6$, $R^7$, $R^8$, $R^9$, or $R^{10}$ is —OH.

2. The compound of claim 1 wherein at least two of $R^6$, $R^7$, $R^8$, $R^9$, or $R^{10}$ are —OH.

3. The compound of claim 2 wherein $R^8$ is —OH, wherein none of $R^1$, $R^2$, $R^3$, $R^4$, $R^5$, $R^6$, $R^7$, $R^9$, or $R^{10}$ are $C_1$-$C_6$ alkoxy.

4. A compound selected from the group consisting of:

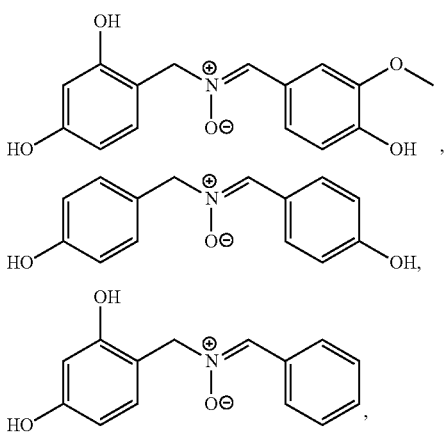

-continued

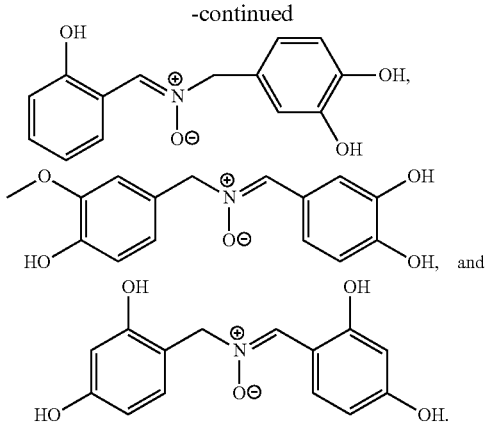

5. The compound of claim 4 wherein the compound is selected from the group consisting of:

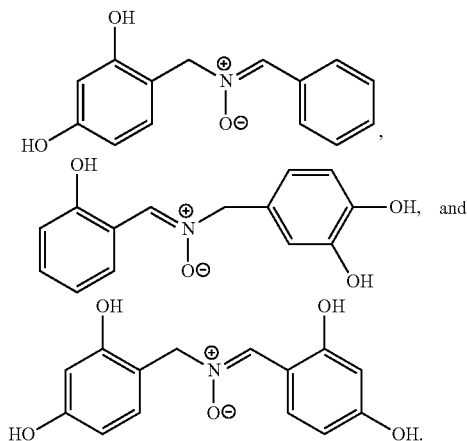

6. A personal care composition comprising:
(a) an antioxidant compound of Formula I:

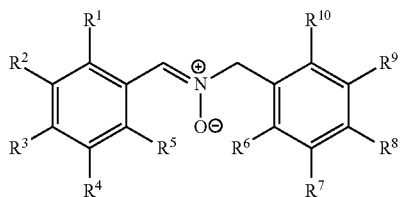

wherein $R^1$, $R^2$, $R^3$, $R^4$, $R^5$, $R^6$, $R^7$, $R^8$, $R^9$, and $R^{10}$ are independently H, $C_1$-$C_{10}$ alkyl, —OH, $C_1$-$C_6$ alkoxy, —COOH, —COO$^-$M$^+$, or —O$^-$M$^+$, where M$^+$ is a sodium, potassium, or ammonium ion, provided that at least three of $R^1$, $R^2$, $R^3$, $R^4$, $R^5$, $R^6$, $R^7$, $R^8$, $R^9$, or $R^{10}$ is —OH, wherein at least one of $R^6$, $R^7$, $R^8$, $R^9$, or $R^{10}$ is —OH; and (b) a dermatologically acceptable carrier.

7. A cosmetic method of treating skin comprising applying to the skin the composition of claim 6.

8. A method for inhibiting the degradation of collagen in skin, the method comprising: topically administering to the skin an effective amount of the composition of claim 6.

9. A method for reducing the visible signs of aging, the method comprising: applying to skin in need of such treatment the composition of claim 6.

10. The composition of claim 6 wherein at least two of $R^6$, $R^7$, $R^8$, $R^9$, or $R^{10}$ are —OH.

11. The composition of claim 6 wherein $R^8$ is —OH, wherein none of $R^1$, $R^2$, $R^3$, $R^4$, $R^5$, $R^6$, $R^7$, $R^9$, or $R^{10}$ are $C_1$-$C_6$ alkoxy.

* * * * *